US00PP28334P3

(12) United States Plant Patent
Mazzardis

(10) Patent No.: US PP28,334 P3
(45) Date of Patent: Aug. 29, 2017

(54) BLUEBERRY PLANT NAMED 'EB 9-4'

(50) Latin Name: ***Vaccinium* hybrid**
Varietal Denomination: EB 9-4

(71) Applicant: Vincent David Mazzardis, Joondalup (AU)

(72) Inventor: Vincent David Mazzardis, Joondalup (AU)

(73) Assignee: Bisa Trading Pty. Ltd., Cannington (AU)

( * ) Notice: Subject to any disclaimer, the term of this patent is extended or adjusted under 35 U.S.C. 154(b) by 18 days.

(21) Appl. No.: 14/756,641

(22) Filed: Sep. 28, 2015

(65) Prior Publication Data

US 2016/0113170 P1 Apr. 21, 2016

(30) Foreign Application Priority Data

Oct. 16, 2014 (AU) ..... PBR 2014/244

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

FOREIGN PATENT DOCUMENTS

AU 2014/244 10/2014

OTHER PUBLICATIONS

Plant Varieties Journal, vol. 28, No. 1.

*Primary Examiner* — Susan McCormick Ewoldt
(74) *Attorney, Agent, or Firm* — Randall Danskin P.S.

(57) ABSTRACT

A new and distinct variety of blueberry plant is described, and which is characterized as to novelty by producing a very large fruit which is mature for harvesting and shipment in the very early season under the ecological conditions prevailing in and near Yanchep Springs, Western Australia.

1 Drawing Sheet

Latin name: '*Vaccinium* hybrid'.
Varietal denomination: 'EB 9-4'.

RELATED APPLICATION DATA

The present application claims priority to Australian Plant Breeders Rights Application, Serial No. 2014/244, and which was filed on Oct. 16, 2014, and was further accepted on Dec. 23, 2014.

BACKGROUND OF THE NEW VARIETY

The present invention relates to a new, novel, and distinct variety of blueberry plant, '*Vaccinium* hybrid' and which has been denominated varietally as 'EB 9-4'.

ORIGIN

The present variety of blueberry plant resulted from an ongoing development program which I have conducted to identify such plants. The purpose of this program is to improve the commercial quality of blueberry plants, and other species. To this end, I have made controlled hybrid cross-pollinations in order to produce plant populations from which improved progeny are evaluated and thereafter selected.

The blueberry plant 'EB 9-4' was originated by me, and selected from a population of new plants growing at my farm, and which is located near Yanchep Springs, in Yanchep, Western Australia. The new variety of blueberry plant was derived from a controlled cross-pollination of the seed parent, blueberry plant 'BB1' [unpatented], and a pollen parent, blueberry plant '99-4' [unpatented], during the 2006 growing season. The seed parent, blueberry parent 'BB-1', is characterized by an upright, bush-type growing characteristic, a mid-season flowering date, and which further produces medium to large, and firm fruit. Still further, the fruit produced by the pollen parent, blueberry plant '99-4' is characterized by a spreading growth habit, an earlier flowering date, and which further produces fruit having a large size. The resulting seed from the seed parent 'BB-1' produced about 500 plants. These new plants, and the fruit produced therefrom, were assessed during the 2008 growing season. A further assessment was conducted in 2009. The subsequent assessment resulted in the selection of blueberry plant, 'EB 9-4' for further asexual propagation. Further, asexual reproduction of the new variety, 'EB 9-4', and the evaluation of the growth habits of the new plant, and the fruit produced thereby, has led me to conclude that 'EB 9-4' is a distinct and new variety of the blueberry plant. Additional vegetative asexual propagation has taken place during the 2010 through 2014 growing seasons. All other asexually reproduced plants have proven to be true to the original new plant. From my perspective, the present, new variety of blueberry plant is considered to be novel in view of its semi-upright bush-type growth habit; large to very large, and slightly flat fruit, and which further has an excellent flavor. The new blueberry plant 'EB 9-4' also displays a very early flowering and fruit maturity dates. The asexual reproduction of Blueberry Plant 'EB 9-4' occurred at Yanchep Springs, Yanchep Western Australia.

In comparison to the seed parent 'BB 1', the present, new variety 'EB 9-4' is distinguishable therefrom by displaying a semi-upright, to intermediate growth habit; a large corolla tube; a sepal form which is considered incurving; a firm fruit texture; and a high fruit sweetness. Still further, the new variety of blueberry plant has a very early date of flowering in relative comparison to the seed parent 'BB-1', and which is considered to flower in the middle of the season. Still further, and in relative comparison to the pollen parent, 'EB 99-4', the present, new variety of blueberry plant is distinguishable therefrom based upon its displayed semi-upright to intermediate growth habit. Further, the fruit produced by the pollen parent '99-4' is considered to be merely large, as opposed to the large and very large fruit produced by the new variety of blueberry plant. In relative comparison to another most closely-related variety, that being the 'Ridley 1111', variety of blueberry plant, now U.S. Plant Pat. No. 23,572 and which was filed on Jan. 18, 2011 the present, new variety of blueberry plant is distinguishable therefrom by producing fruit which are considered large to very large in comparison to the medium sized fruit produced by the 'Ridley 1111' blueberry plant. The aforementioned asexual propagation of the present plant was accomplished by me by means of cuttings. My observations of the new and novel plant over a number of years has confirmed the plant characteristics of the present variety across these multiple generations which are mentioned in the paragraphs, above.

BRIEF DESCRIPTION OF THE DRAWINGS

The accompanying drawing, which is provided, is a color photograph of the new blueberry plant 'EB 9-4', at an age of two (2) years, and which further shows the new variety 'EB 9-4' juxtaposed relative to one of the closest-known varieties, that being the blueberry plant 'EB 8-1', now U.S. Plant Pat. No. 25,859 and which was filed in the U.S. Patent and Trademark Office on Jun. 12, 2013. The photograph as provided shows a portion of a vegetative stem showing the growth habit of the leaves. One leaf is further displayed showing the dorsal coloration thereof, and the relative sizes of several fruit are depicted showing both the dorsal and ventral coloration, as well as the morphology of same. The photograph additionally shows the same portions of the closest known plant, that being, the blueberry plant 'EB 8-1', for comparative purposes. The color in this photograph is as nearly true as is possible in a color representation of this type. Due to chemical development, processing, and printing, the leavers and fruit depicted in this photograph may, or may not, be accurate when compared to the actual specimen. For this reason, future color references should be made to the color plates and descriptions provided, hereinafter. Common color names are also occasionally employed.

NOT A COMMERCIAL WARRANTY

The following detailed descriptions were prepared to solely comply with the provisions of 35 U.S.C. §112, and do not constitute a commercial warranty, (either expressed or implied), that the present variety will, in the future, display all the botanical, horticultural or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

Plant:

*Plant vigor*.—Generally considered average for the species. The age of the plant at the time of the description that follows herein is three (3) years. The colors and codes used herein to describe the Blueberry Plant named 'EB 9-4', refer to The Royal Horticultural Society (R.H.S.) Colour Chart, 5$^{th}$ Ed., 2007.

*Plant growth habit*.—Considered semi-upright to intermediate. This is in contrast to the closest-known variety 'EB 8-1', and which has a semi-spreading growth habit, and further, in contrast to the seed parent 'BB 1', and which has an upright, bush-type growth habit. Still further, the pollen parent, blueberry plant '99-4', has a spreading growth habit.

*Color*.—One Year Old Shoots — Yellow Green N144C (R.H.S. Colour Chart, 5$^{th}$ Ed., 2007).

*Internode length*.—One Year Old Shoots — Considered long for the species, about 18 mm. This is in contrast to the closest-known variety, blueberry plant 'EB 8-1' and which is just considered average, and sometimes occasionally long. Height of plant at time of description is about 1.3 m. Width of plant at time of description is about 1 m.

*Bark color*.—Greyed Orange 177B (R.H.S. Colour Chart, 5$^{th}$ Ed., 2007).

Leaves:

*Leaf length*.—Considered short, or sometimes average in length, as compared to the closest-known variety 'EB 8-1'. In this regard, the leaf length of the new variety is about 67.47 mm.

*Leave width*.—Considered average for the species, about 29.10 mm.

*Leaf ratio*.—Length/Width — Considered average for the species.

*Leaf shape*.—Elliptic.

*Leaf color*.—Dorsal Surface — Green 137A (R.H.S. Colour Chart, 5$^{th}$ Ed., 2007).

*Leaf color*.—Under Surface: Yellow Green 147B (R.H.S. Colour Chart, 5$^{th}$ Ed., 2007).

*Texture of the leaf*.—Glabrous.

*Leaf apex shape*.—Acute.

*Leaf apex base shape*.—Acute.

*Vein color of the leaf*.—Yellow Green 145B (R.H.S. Colour Chart, 5$^{th}$ Ed., 2007).

*Venation pattern of the leaf*.—Pinnately reticulate.

*Leaf arrangement*.—Alternate.

*Leaf color intensity*.—Dorsal Surface — Considered dark green. This is in relative comparison to the medium to dark colored green as displayed by the leaves of the closest-known blueberry variety 'EB 8-1'.

*Leaf marginal edge*.—Entire.

*Seed color*.—Greyed Orange 168C (R.H.S. Colour Chart, 5$^{th}$ Ed., 2007).

Flowers:

*Flower bud coloration*.—The Anthocyanin coloration is considered very weak in the present variety.

*Inflorescence length*.—About 21 mm, this is considered medium to long for the species. This is in contrast to the closest-known variety which is considered merely average.

*Color of opened flower*.—White 155C (R.H.S. Colour Chart, 5$^{th}$ Ed., 2007).

*Average number of flowers per inflorescence is*.—Twelve (12).

*Corolla texture*.—Rigid.

*Corolla length*.—About 9.8 mm.

*Corolla diameter*.—About 9.4 mm.

*Corolla color*.—White 155C (R.H.S. Colour Chart, 5$^{th}$ Ed., 2007).

*Corolla aperture size*.—About 4.4 mm.

*Pedicle length*.—About 5.8 mm.

*Pedicle color*.—Yellow Green 145B (R.H.S. Colour Chart, 5$^{th}$ Ed., 2007). This new and novel variety of Blueberry plant named EB 9-4 is an evergreen, and therefor it continuously sets buds, flowers and fruits for the duration over the whole year and has an approximately 75 day fruit development period in the specified location of culture.

*Corolla shape*.—Urceolate.

*Corolla tube size*.—Considered large for the species. This is in contrast to the average sized corolla tube as seen upon the closest-known variety 'EB 8-1'.

*Corolla tube coloration*.—The anthocyanin coloration of the corolla tube is either absent or very weak.

*Corolla tube ridges*.—Present.

Fruit:

*Fruit cluster density*.—Considered average.

*Color intensity*.—Unripe fruit — Yellow Green 145A (R.H.S. Colour Chart, 5$^{th}$ Ed., 2007).

*Fruit size*.—Generally large to very large. This is in comparison to the closest-known variety 'EB 8-1', and which produces large fruit; and the seed parent 'BB 1' that produces medium-large sized fruit. In this regard, the average fruit diameter is about 24.52 mm. in comparison to the closest-known variety, 'EB 8-1', and which has fruit diameter of about 20.72 mm. Still further the fruit height of the new variety of blueberry plant is, on average, about 14.20 mm.

*Fruit shape when viewed in a longitudinal perspective*.—Considered oblate.

*Sepal position*.—Generally considered semi-erect.

*Sepal type*.—Generally considered incurving. This is in contrast to the same displayed characteristic of the closest-known variety, 'EB 8-1', and wherein the sepal type is considered straight.

*Calyx basin diameter*.—Considered small. In this regard, the Calyx basin diameter is about 9.58 mm; and the Calyx basin depth is about 3.22 mm.

*Fruit weight*.—On average about 4.67 gm. In contrast, the closest-known variety, 'EB 8-1', produces fruit which, on average, weighs about 4.05 gm.

*Intensity of bloom*.—Considered quite strong for the species.

*Fruit skin color*.—Black 203C (R.H.S. Colour Chart, 5$^{th}$ Ed., 2007).

*Fruit flesh color* (*ripened fruit*).—Yellow Green 144D (R.H.S. Colour Chart, 5$^{th}$ Ed., 2007).

*Fruit firmness*.—Generally considered firm. This is in contrast to the closest-known variety 'EB 8-1', and which displays an average fruit firmness.

*Fruit sweetness*.—Generally — The present variety is considered a very sweet fruit in contrast to the average sweetness as displayed by the closest-known variety, 'EB 8-1'.

*Fruit acidity*.—Generally considered low to medium for the species.

*Plant fruiting type*.—Fruiting typically is observed on one-year old, and current season's shoots.

*Resistance to insects and disease*.—No particular susceptibilities were noted. The present variety has not been tested to expose or detect any susceptibilities or resistances to any known plant and/or fruit diseases.

Reproductive organs of the plant:

*Size of the pollen anthers*.—About 7.0 mm.

*Color of the pollen anthers*.—Greyed Orange N157B (R.H.S. Colour Chart, 5$^{th}$ Ed., 2007).

*Pistil length*.—About 9.2 mm.

*Pistil color*.—Yellow Green 145B (R.H.S. Colour Chart, 5$^{th}$ Ed., 2007). Market use of the fruit is First Grade Fresh Market Fruit.

*Pollination requirement*.—Self-fertile.

Fruit productivity:

*Average weight of fruit*.—About 4.67 g. Storability of the plant fruit is considered to be long. The observed date of the first pick is approximately February in the specified location of culture. The observed date of the last pick is approximately February of the following year in the specific location of culture.

Although the new variety of blueberry plant possesses the described characteristics when grown under the ecological conditions prevailing near Yanchep Springs, Western Australia, it should be understood that variations of the usual magnitude and characteristics incident to changes in growing conditions, fertilization, pruning, pest control, frost, climatic variables, and horticultural management are to be expected.

Having thus described and illustrated my new variety of blueberry plant, what I claim is new, and desire to secure by Plant Letters Patent is:

1. A new and distinct variety of blueberry plant as substantially shown and described, and which is denominated varietally as 'EB 9-4', and which further produces a large to very large fruit which is mature for harvesting and shipment in the very early season under the ecological conditions prevailing near Yanchep Springs, Western Australia.

* * * * *

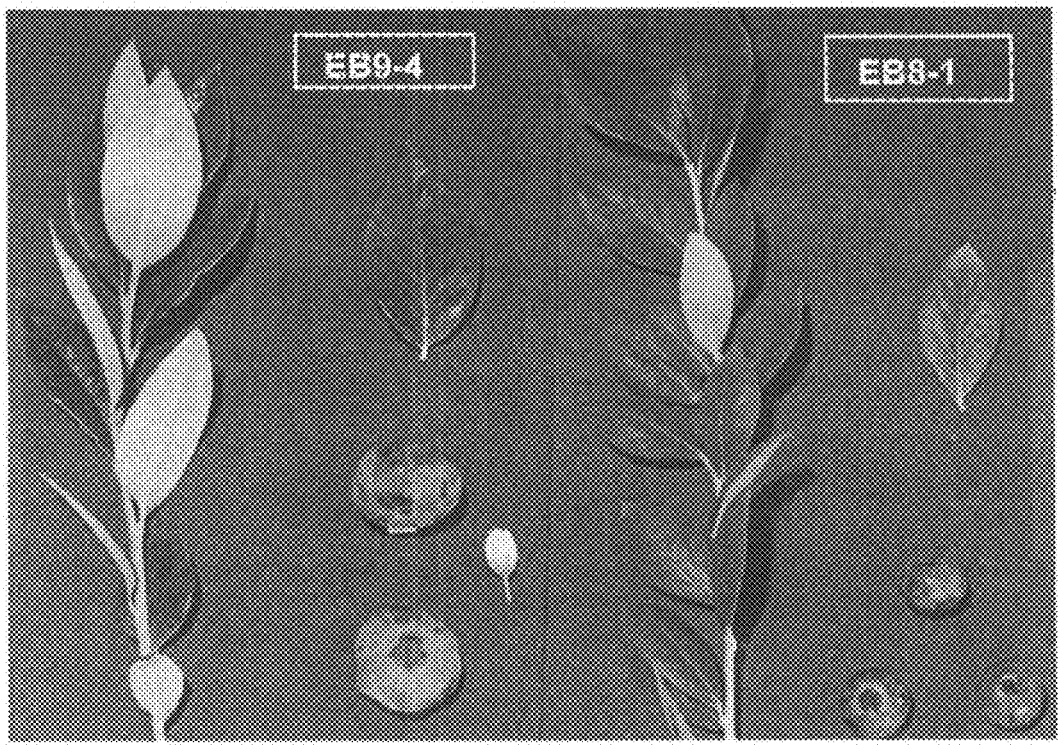
EB9-4
EB8-1